US006589189B2

(12) United States Patent
Meyerson et al.

(10) Patent No.: US 6,589,189 B2
(45) Date of Patent: Jul. 8, 2003

(54) NON-INVASIVE METHOD AND APPARATUS FOR MONITORING INTRACRANIAL PRESSURE

(75) Inventors: Scott C. Meyerson, Mounds View, MN (US); Paul Alexandre Avan, Chamalieres (FR); Bela Buki, Krems (AT)

(73) Assignee: Rice Creek Medical, LLC, Mounds View, MN (US)

( * ) Notice: Subject to any disclaimer, the term of this patent is extended or adjusted under 35 U.S.C. 154(b) by 0 days.

(21) Appl. No.: 09/755,158

(22) Filed: Jan. 5, 2001

(65) Prior Publication Data

US 2001/0027335 A1 Oct. 4, 2001

Related U.S. Application Data

(60) Provisional application No. 60/175,099, filed on Jan. 7, 2000.

(51) Int. Cl.[7] .................................................. A61B 5/00
(52) U.S. Cl. ....................................... 600/561; 600/559
(58) Field of Search ................................. 600/438, 561, 600/559; 381/60; 607/56, 57

(56) References Cited

U.S. PATENT DOCUMENTS

| 3,872,858 | A | | 3/1975 | Hudson et al. |
|---|---|---|---|---|
| 4,043,321 | A | | 8/1977 | Soldner et al. |
| 4,141,348 | A | | 2/1979 | Nidman |
| 4,186,751 | A | | 2/1980 | Fleischmann |
| 4,204,547 | A | | 5/1980 | Allocca |
| 4,374,526 | A | | 2/1983 | Kemp |
| 4,564,022 | A | | 1/1986 | Rosenfeld et al. |
| 4,690,149 | A | | 9/1987 | Ko |
| 4,819,648 | A | | 4/1989 | Ko |
| 4,841,986 | A | | 6/1989 | Marchbanks |
| 4,884,447 | A | | 12/1989 | Kemp et al. |
| 4,971,061 | A | | 11/1990 | Kageyama et al. |
| 4,984,567 | A | * | 1/1991 | Kageyama ................... 600/438 |
| 5,074,310 | A | | 12/1991 | Mick |
| 5,117,835 | A | * | 6/1992 | Mick ........................... 600/561 |
| 5,388,583 | A | | 2/1995 | Ragauskas et al. |
| 5,411,028 | A | | 5/1995 | Bonnefous |
| 5,617,873 | A | * | 4/1997 | Yost et al. ................... 600/561 |
| 5,664,577 | A | * | 9/1997 | Lonsbury-Martin et al. ........................... 600/559 |

(List continued on next page.)

FOREIGN PATENT DOCUMENTS

| EP | 09 330 61 A1 | 8/1999 |
|---|---|---|
| WO | WO 97/30630 | 11/2000 |

OTHER PUBLICATIONS

Buki, et al., "Otoacoustic Emissions: A New Tool for Monitoring Intracranial Pressure Changes Through Stapes Displacements," *Hearing Research* 94 (1996) 125–139; Elsevier Science B.V., Jan 5, 1996.

Buki, et al., "Middle–ear Influence on Otoacoustic Emissions. II: Contributions of Posture and Intracranial Pressure," *Hearing Research* 140 (2000) 202–211; Elsevier Science B.V., Oct. 26, 1999.

*Primary Examiner*—Francis J. Jaworski
(74) *Attorney, Agent, or Firm*—Fredrikson & Byron, P.A.

(57) ABSTRACT

An intracranial pressure (ICP) monitoring system and method for using such is disclosed. The system stimulates and interprets predictable external effects of elevated ICP. In one embodiment, the system non-invasively and continuously monitors ICP by stimulating and interpreting predictable changes measured in the otoacoustic emission (OAE) signal of the patient. The system may alternately non-invasively and continuously monitor ICP by stimulating, measuring, and interpreting other responses which rely on the transmission of vibrations through the middle ear cochlear interface, such as tympanograms (TGRAMs), ocular-acoustic reflex, auditory brainstem response (ABR), or cochlear microphonics.

81 Claims, 8 Drawing Sheets

U.S. PATENT DOCUMENTS

| | | | |
|---|---|---|---|
| 5,699,809 A | * 12/1997 | Combs et al. | ............... 600/558 |
| 5,792,073 A | 8/1998 | Keefe | |
| 5,840,018 A | 11/1998 | Michaeli | |
| 5,919,144 A | * 7/1999 | Bridges et al. | ............. 600/561 |
| 5,951,477 A | 9/1999 | Regauskas et al. | |
| 5,993,398 A | 11/1999 | Alperin | |
| 6,086,533 A | 7/2000 | Madsen | |
| 6,117,089 A | 9/2000 | Sinha | |
| 6,146,336 A | 11/2000 | Paulat | |
| 6,231,509 B1 | * 5/2001 | Johnson et al. | ............. 600/438 |
| 6,248,080 B1 | 6/2001 | Miesel et al. | |

* cited by examiner

NON-INVASIVE METHOD AND APPARATUS FOR MONITORING INTRACRANIAL PRESSURE

This application claims the benefit of U.S. provisional application No. 60/175,099, Jan. 7, 2000.

FIELD OF THE INVENTION

The present invention relates generally to intracranial pressure (ICP) monitoring. Specifically, the invention relates to a method and apparatus of non-invasively, without requiring a breach of the skin, skull, or dura, monitoring ICP. More specifically, the invention provides a method and apparatus for stimulating and interpreting predictable external effects of elevated ICP such as changes in cochlear impedance coupling to monitor ICP. In one embodiment, the system non-invasively and continuously monitors ICP by stimulating and interpreting predictable changes measured in the otoacoustic emission (OAE) signal of the patient.

BACKGROUND OF THE INVENTION

Intracranial pressure is closely related to cerebral perfusion (blood flow in the brain). Elevated ICP reduces cerebral perfusion pressure (CPP), and if uncontrolled, results in vomiting, headaches, blurred vision, or loss of consciousness, escalating to permanent brain damage, and eventually a fatal hemorrhage at the base of the skull. Increased ICP is a medical/surgical emergency. Particular instances where it is desirable to monitor ICP are in traumatic brain injury (TBI) victims, stroke victims, hydrocephalus patients, and patients undergoing intracranial procedures, "shaken baby" syndrome, kidney dialysis, or artificial liver support. Current methods of monitoring ICP are typically invasive, expensive, and/or difficult to perform outside of a hospital setting.

Traumatic Brain Injury

An estimated 1.75 million TBI's occur annually (extrapolated from 1,540,000 TBI's in 1991) in the United States. The U.S. Department of Education, National Institute on Disability and Rehabilitation Research in conjunction with 17 TBI research hospitals around the U.S. have established a set of indicators for classification of TBI:

1) Documented loss of consciousness for an unspecified time;
2) Amnesia for the event. No recall of the actual trauma;
3) A Glasgow Coma Scale (GCS) score of less than 15 during the first 24 hours.

Of these indicators, amnesia assessment is a preferred indicator of TBI severity. Amnesia of one day is considered moderate, while one month of amnesia indicates severe TBI. Although amnesia is a good indicator of TBI severity and a reasonable predictor of long term outcomes, this slow evaluation method provides no help in emergency response to patient diagnosis or treatment.

The GCS is a TBI severity assessment system using subjective observations in three basic categories: eye opening (E), best motor response (M), and verbal response (V). A patient's GCS score is the sum of the patients E, B, and V scores. This sum ranges from 3 to 15 with 3 indicating severe TBS and 15 indicating no or very mild TBS. The non-invasive nature of CT scans make them a very common procedure for TBI patients whose GCS score is mild or moderate, but the data is slow and expensive. The patient must be brought to the equipment and, in many cases, the patient cannot be immediately moved. The cost is compounded because CTs do not provide direct assessment of ICP (two or more scans are required to assess trends) and in 9–13% of patients, the CT will be normal even with elevated ICP. Due to the invasiveness of current ICP monitoring procedures, the general practice is to not start invasive ICP monitoring unless the patient's GCS score is less than or equal to 8, at which time the drawbacks of the procedure are outweighed by the severity of patient condition. This means 90% of hospitalized TBI patients are assessed only with GCS and possibly a CT scan. Significant rehabilitation problems have resulted in patients with mild or moderate GCS scores, highlighting the need for non-invasive ICP monitoring techniques. GCS assessment and CT scans are helpful, but clearly point out the time-sensitive need for more direct data.

Stroke

First time strokes can unpredictably lead to brain swelling. Strokes are divided into two main categories, (1) hemorrhagic (the bursting of a cerebral blood vessel), and (2) the more common ischemic (the blockage of a cerebral blood vessel). Correct diagnosis of the stroke type is critical because the clot-dissolving drug t-PA (and analogs), used to treat ischemic strokes, is contraindicated for hemorrhagic strokes. Furthermore, the diagnosis of stroke type is time critical because starting t-PA treatment more than 3 hours after stroke could result in a higher rate of bleeding into the brain. Approximately 80% of all strokes each year are ischemic. ICP in this type of stroke initially remains low, but elevates as the loss of blood traumatizes the brain. ICP will also elevate when the clot is removed and blood flow is restored. Hemorrhagic strokes involve the direct complication of elevated ICP.

Hydrocephalus

Ventroperneal shunts are implanted to treat hydrocephalus. A CT scan cannot be used for patients with hydrocephalus because the ventricles of the brain commonly remain swollen even with normal ICP, and the risk of invasive systems cannot be justified. Diagnosis of shunt system problems are currently based on symptoms reported by the patient or caregiver and are thus subjective. OAE is stable over a period of months and an ICP baseline could be stored for these patients and compared with measurements during future visits. Current ICP measurement technology does not provide adequate means for treating patients with hydrocephalus because of the possible inaccurate readings and the risk inherent in invasive measurement procedures.

Intracranial Procedures

There is a current medical need for ICP monitoring for patient recovering from elective intracranial surgery. A retrospective study found elevated ICP postoperatively in 17% of patients who underwent supratentorial or infratentorial surgery. Of these, over one fourth experienced clinical symptoms latent or concurrent to ICP elevation. Medical personnel need to be able to identify these patients and administer therapy before any clinical symptoms are detected. It is interesting to note that during the study, which used invasive methods to measure ICP, the infection rate was 1.2%, highlighting the risk of invasive ICP monitoring.

Laparoscopic and Abdominal Insulflation

Laparoscopic procedures are often performed requiring abdominal insulflation concomitant with Trendelenburg (head down tilt) position. The combination of anesthetic, body position, and insulflation can substantially elevate ICP. Due to the prohibitive additional cost and risk, routine ICP monitoring during these procedures is not done. However, there is growing concern about elevated ICP during these procedures.

Liver and Kidney Support

There is a current medical need to assess ICP variation in patients who are in the latter stages of liver failure and require external liver support (i.e. artificial liver). As the liver fails, toxins build up in the body and this build up generally causes elevation of ICP. One measure of liver function (or therapy function) is to monitor ICP. As toxins build, ICP increases, thus allowing the physician (and possibly the patient) to anticipate when the next therapy session should commence. While on the artificial liver machine, toxins are removed, and ICP should fall, providing an indication of therapy function. A similar situation exists for patients being treated for kidney failure, either by hemodialysis or peritoneal dialysis.

Others

Additional causes for an increase in ICP include the following: meningitis, encephalitis, intracranial abscess, hemorrhage, shunt blockage, tumors, Reye's Syndrome, "shaken baby" syndrome, and benign intracranial hypertension.

Normal intracranial pressure (ICP) for adults is between 5 mm/Hg and 15 mm/Hg. When ICP level is considered abnormal is controversial, however, it becomes a concern as it rises higher than 20 mm/Hg.

ICP is closely related to cerebral perfusion (blood flow in the brain). To a first approximation, the cerebral perfusion pressure (CPP) is the difference between an individual's arterial blood pressure (ABP) and intracranial pressure (ICP). Thus, approximately, CPP=ABP–ICP. If one assumes ABP to be constant, then an increase in ICP results in less blood flow to the brain. Because of this relationship, and the difficulty of measuring CPP directly, ABP and ICP are often measured to assess CPP. In a healthy individual, automatic regulation mechanisms in the body keep ABP, ICP, and thus CPP within a normal range. These automatic regulation systems are often non-functional in brain trauma, stroke, hydrocephalic patients, and patients with liver or kidney failure, so that monitoring and management of ICP becomes a critical aspect of medical care. In addition, during surgeries such as abdominal laparoscopy, cardiac bypass, and following any type of cranial surgery, continuous, non-invasive monitoring of ICP, if it were economically and technically feasible, would be beneficial. Elevated ICP reduces CPP, and if uncontrolled, results in vomiting, headaches, blurred vision, or loss of consciousness, escalating to permanent brain damage, and eventually a fatal hemorrhage at the base of the skull.

Current ICP monitoring techniques are generally grouped as either invasive and non-invasive. The invasive group is further divided into soft tissue, for example lumbar puncture, and bone drilling procedures, for example subarachnoid screws or plugs, subdural catheters, and ventriculostomy catheters.

Lumbar Puncture

In a lumbar puncture or spinal tap, a clinician delicately passes a fine needle through the lower region of the back into the fluid of the spinal cord. Once the spinal spaces have been penetrated, ICP can be estimated by attaching a pressure sensor. The communication between the fluid in the spinal column and the cranium allows the physician to ascertain the pressure in the cranium. Though invasive, a lumbar puncture is sometimes preferred because it is a soft tissue procedure rather than a cranial procedure. Generally, a non-neuro clinician will not feel comfortable performing a cranial procedure, but will perform a lumbar puncture. This procedure does allow transient manipulation or sampling of the intracranial fluid system, but is often painful and many times results in after affects, and always raises patient apprehension. It is a short term procedure and is generally not considered for long term ICP monitoring.

Cranial ICP Assessment Methods

There are five common current invasive methods of measuring ICP which breach the skull: ventriculostomy, intraparenchymal fiberoptic catheter, epidural transducer, subdural catheter, and subdural bolt. These have varying degrees of invasiveness. A subarachnoid screw involves inserting the screw in a hole which has been drilled through the skull bone, but does not breach the dura. Such systems can be threaded like a screw, or just a "friction fit" plug. A subdural catheter involves inserting the catheter a hole in the skull and dura, and squeezing the catheter between the dura and the brain itself. Ventriculostomy catheters are inserted through a hole drilled in the skull and dura, and are blindly forced through the gray matter such that the tip of the catheter is positioned in one of the cranial ventricles.

Of these methods, only a ventriculostomy can also be used to deliver therapy, which is usually draining fluid from the ventricles. The epidural approach has the lowest complication rate, but all suffer gradual loss of accuracy. The failure mechanism is stiffening of the dura and/or localized hematomas at the monitoring site. This known degradation starts immediately after implant and will make the transducer unreliable anywhere from 1 to 3 weeks post implant.

This invasive group, although medically accepted and routinely used, suffers several drawbacks. The transducer has to be calibrated in some fashion before insertion. The placement of the system requires a highly trained individual; in almost all clinical settings, this procedure is limited to physicians, and in most cases further limited to a specialist such as a neurosurgeon. This generally limits these procedures to larger medical facilities. Furthermore, there is a relatively short term (32–72 hours) reliability and stability of the system, either because of leaks or plugging of the transducer, or inadvertently being disturbed, or even being pulled out. This concern generally limits these procedures to a more intense monitoring setting such as an ICU. There are also associated risks of transducer placement such as brain or spinal cord damage and infection. Even though these risks are low, these concerns generally limit the group of non-invasive ICP monitoring techniques to the hospital setting and prevents standard use of the techniques in clinic or nursing home settings.

In the non-invasive group, the accepted, commercially available method of monitoring ICP consists of taking a CT or other image of the head, interpreting the image and observing changes in various features. This method requires a high level of skill to read and assess the images and requires that the patient be brought to the imaging equipment. In many cases, a scan is delayed or put off simply because the patient is not stable enough to be moved. Even after the patient is stable, the various tubes and equipment connections to the patient have to be accounted for during the trip to the CT, and many times additional personnel are required, with a respective increase in cost. In addition, the scans themselves are single measurements—"snap-shots" in time, of which at least two are required to assess subtle-changes and variations. A 'series' of scans could approximate continuous monitoring, but is not economically practical.

Other non-invasive ICP monitoring techniques have been developed. A non-invasive ICP monitoring system is taught in U.S. Pat. No. 4,841,986 to Marchbanks. This system is based on fine volume measurements of the external auditory canal during elicitation of the human stapedial reflex. The concept is that at normal ICP, the stapedial reflex will pull on the stapes, resulting in distortion of the tympanic membrane (ear drum). This will define a volume for that ICP level. As ICP increases, the stapes will be pushed away from the cochlea, and the stapedial reflex will pull on the stapes differently, resulting in a different distortion of the tympanic membrane, which can be measured as a delta volume. This system requires a rather loud sound to be output in the patients ear. Severe ambient noise and sealing constraints are inherent in the technology which lead to a cumbersome and time consuming setup. The system has a non-linear response, acting much like a threshold function.

A compliance measuring system taught by Paulat in EP 0933061A1 measures changes in ICP. The system uses micro volume measurements in the auditory canal similar to the Marchbanks system. The system detects the fine volume changes as the time varying ICP waves are communicated to the cochlea via the cochlear aqueduct, through the ossicles to the tympanic membrane. This device is AC coupled so it cannot monitor ICP changes over time (i.e. mean ICP values). It has been proposed that frequencies greater than 10 Hz could not be communicated via the cochlear aqueduct. Stated another way, respiration and heart rate frequencies may not be transmitted through the cochlear aqueduct.

In Bridger in U.S. Pat. No. 5,919,144, a non-invasive system is disclosed based on real-time analysis of acoustic interaction with the brain and changes in tissue acoustic properties as ICP changes.

Other non-invasive techniques include:

- electro-magnetic techniques taught by Ko in U.S. Pat. Nos. 4,690,149 and 4,819,648, by Alperin in U.S. Pat. No. 5,993,398, and Paulat in U.S. Pat. No. 6,146,336;
- ultra sonic or vibratory techniques such as U.S. Pat. No. 3,872,858 to Hudson et al., U.S. Pat. No. 4,043,321 to Soldner et al., U.S. Pat. Nos. 4,971,061 and 4,984,567 to Kageyama et al., U.S. Pat. Nos. 5,074,310 and 5,117,835 to Mick, U.S. Pat. Nos. 5,388,583 and 5,951,477 to Ragauskas et al., U.S. Pat. No. 5,411,028 to Bonnefous, U.S. Pat. No. 5,617,873 to Yost et al., U.S. Pat. No. 5,840,018 to Michaeli, U.S. Pat. No. 6,086,533 to Madsen, and U.S. Pat. No. 6,117,089 to Sinha;
- jugular vein occlusion taught by Allocca in U.S. Pat. No. 4,204,547;
- ocular latency in U.S. Pat. No. 4,564,022 to Rosenfeld et al.

Another system stated to be "non-invasive" is described in U.S. Pat. No. 4,141,348 to Hittman and companion U.S. Pat. No. 4,186,751 to Fleischmann. This nuclear powered pressure sensor was not grouped with the other non-invasive systems because it is designed to be implanted totally under the scalp of the patient.

Each of the currently used and medically accepted methods of ICP assessment are deficient in some way, and all require a high skill level to administer. Because of the deficits in current measurement methodologies, there is a need for a non-invasive, easily administered, long-term, continuous assessment of ICP.

SUMMARY OF THE INVENTION

To address the difficulties noted above, it is an object of this invention to provide a continuous intracranial pressure monitoring system that is non-invasive and easily administered. The ICP monitoring system of the current invention stimulates and interprets predictable external effects of elevated ICP. In a preferred embodiment, the system non-invasively and continuously monitors ICP by stimulating and interpreting predictable changes measured in the otoacoustic emission (OAE) signal (transient, or cubic distortion) of the patient. The system may alternately non-invasively and continuously monitor ICP by stimulating, measuring, and interpreting other responses which rely on the transmission of vibrations through the middle ear cochlear interface, such as tympanograms (TGRAMs), ocular-acoustic reflex, auditory brainstem response (ABR), or cochlear microphonics. It should be apparent to those skilled in the art that other suitable measurements could be used in monitoring the ICP level. The measurements could be used individually, in conjunction with one another, or in concert with current invasive ICP measuring systems. One, two, or more of the above mentioned measurements may be used in concert with one, two, or more of heart rate, respiration rate, pulse oximeter, blood pressure, or other conventional 'vital signs' measurements.

The portability and ease of the invention enables more frequent ICP assessment in the areas identified previously as well as expansion of ICP assessment into areas heretofore considered economically or technically unfeasible. These new areas include first responders such as EMT's, medics, ambulances, and law enforcement officers; long term care situations such as nursing homes, assisted living, and home care; athletic trainers (during, for example, concussion assessment), and military battlefield application.

In a preferred embodiment, the invention provides a system which utilizes predictable changes in OAE signals to assess and record changes in ICP over time—a system which is compact enough to be strapped to the patients' arm during ambulance or other transport. This system allows EMT's or other first responders to start monitoring changes in ICP, requiring only simple interface(s) to the patient. Examples of these simple interfaces include, but are not limited to; a plug transducer or tube inserted into the patients ear; pulse oximeter type clip on the finger or ear lobe; a stretchy band about the thorax to detect respiration. After arriving at the hospital or trauma center, the ICP history can be downloaded. Starting ICP monitoring early advantageously provides ER physicians expanded and prior time history of the patients changes in ICP to assist in diagnosis and treatments decisions. Many times a patient arrives at a health care facility with no apparent symptoms and is sent home, only to succumb to symptoms of elevated ICP later, resulting in another emergency transport to the hospital.

Another scenario where the invention is especially useful is for a non-symptomatic patient with a known head trauma arriving at a small regional health care facility with no neuro related specialists on staff. Currently, the ER physician is confronted with the decision to; send the patient to a larger facility via ground transport, wait and monitor the patient and if their condition deteriorates, or send the patient to a larger facility via air ambulance. With the present invention, the ER physician is provided with time history of the changes in ICP before sending the patient to a larger facility or home. The device can also be sent home with the non-symptomatic patient to continue ICP monitoring. By home monitoring following a possible brain trauma, a second emergency trip back to the hospital can be avoided.

In another embodiment, the invention is used in conjunction with an invasive pressure transducer such as a sub-arachnoid screw, or lumbar puncture, and the stored ICP data is characterized and quantified based on this reference. This is also used as a reference for future stored data. The pressure transducer interface may be incorporated within the invention apparatus, or a connection from the invention to a current pressure measuring system could be made using a wired or wireless (IR, RF, etc.) means. Also contemplated is the direct entry of the 'reference' pressure via keypad or other entry system.

In another embodiment, the invention is used as a continuous bedside monitor—a system which is portable in terms of size, weight, and power. This allows ICP monitoring to be started on a patient pre-operatively and follow the patient as the patient is moved to the operating room, recovery room, and hospital room. This advantageously allows physicians to monitor ICP during and following cranial, laparoscopic, or other procedures.

In another embodiment, a 'template' of the patients normal ICP signal is captured and stored in the invention, and sent home with the patient, home care provider (parents or other guardians) or long term care provider (i.e. nursing homes). This allows the monitoring of the patients' ICP to be continued following hospital or clinic discharge. This advantageously reduces the cost of long term ICP monitoring by moving the patient from the hospital setting to the nursing home setting, and makes periodic or even continuous ICP monitoring by home care givers economically feasible.

Hydrocephalic infants, brain trauma, or stroke survivors who cannot communicate internal symptoms can be monitored at a greatly reduced cost, yet without increasing risk to the patient. This is also advantageous in the clinical follow up of shunted patients since their ventricles remain swollen even under 'normal' ICP, rendering CT assessment of ICP worthless. Physicians would like to know the ICP of the patient, but are unwilling to subject the patient to an invasive procedure.

An aspect of the invention, which may be included in any of the embodiments, involves other signals (such as pulse rate, blood pressure, oxygen saturation, respiration rate, etc.) measured either as part of the apparatus of the invention, or measured and communicated by other equipment. The additional signals are analyzed in concert with the ICP data to further characterize and qualify the data.

Another aspect of the invention, which may be included in any of the embodiments, is to combine ICP and pulse oximeter (or other suitable measurement) inputs to provide an estimate of cerebral oxygenation.

Another aspect of the invention, which may be included in any of the embodiments, is to combine ICP and blood pressure (or other suitable measurement) inputs to provide the physician with an estimate of cerebral perfusion pressure (CPP).

Another aspect of the invention, which may be included in any of the embodiments, is an accelerometer or other suitable position sensor which is incorporated within the invention to compensate or otherwise offset the postural influences in ICP measurements.

Another aspect of the invention, which may be included in any of the embodiments, is to measure ICP using both ears and provide hemispheric information to the physician.

Another aspect of the invention, which may be included in any of the embodiments, includes a noise canceling system to enhance the signal to noise ratio (SNR) of the ICP signal.

Another aspect of the invention, which may be included in any of the embodiments, synchronizes the ICP measurement to the same phase of the cardiac rhythm or respiration rhythm, or both, to improve the SNR of the ICP signal.

Another aspect of the invention, which may be included in any of the embodiments, synchronizes the ICP measurement to the same phase of the cardiac rhythm or respiration rhythm, or both, to assess the patency of the cochlear aqueduct.

Another aspect of the invention, which may be included in any of the embodiments, is to measure the ICP synchronized to at least two known phases of the cardiac rhythm or respiration rhythm, or both, preferably at diastole and systole/inhalation and expiration, and use that delta to further quantify the ICP reading.

Another aspect of the invention, which may be included in any of the embodiments, is to measure the ICP synchronized to cardiac diastole and systole and/or respiration inhalation and expiration in at least two distinct ICP levels, the levels being manipulated by head tilt, or forced by some chemical means, such as ingestion of glycol. This allows at least 4 different ICP readings, and can be used to further qualify and quantify the ICP reading.

Another aspect of the invention, which may be included in any of the embodiments, is to measure the ICP using OAEs around 2 khz to assess the presence of non-equalized middle ear pressure which can distort or mask the ICP signal in OAE's.

DETAILED DESCRIPTION OF THE DRAWINGS

Figure 7:
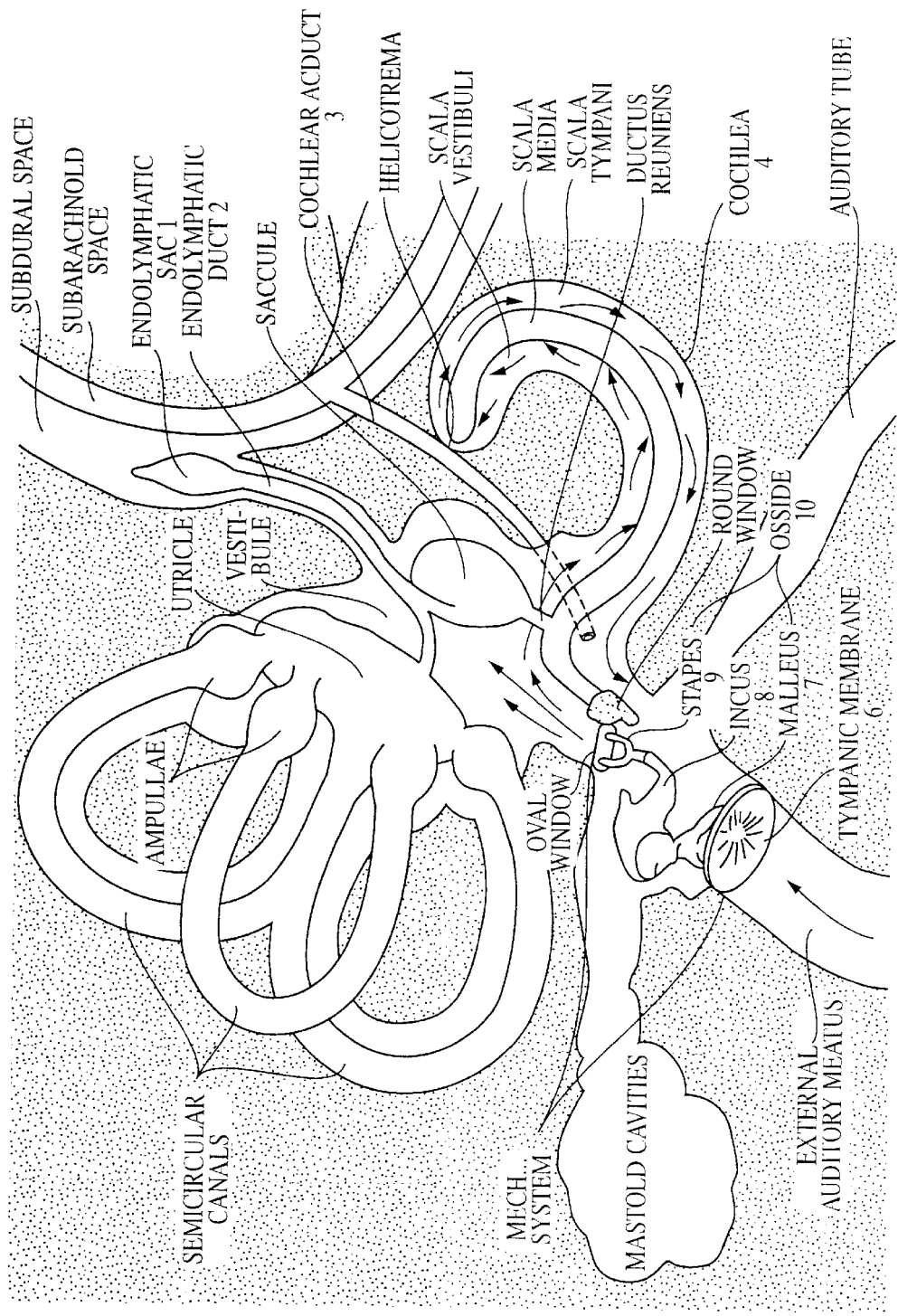
FIG. 7 is a drawing of the anatomy of the ear and surrounding cranial spaces showing the communication between the cranial spaces and the cochlea.

FIG. 7 generally depicts the anatomy of the ear and surrounding cranial spaces. During normal hearing, auditory stimuli enter the external auditory meatus 5 and cause tympanic membrane 6 to vibrate. The vibrations are communicated through the ossicular chain 10 (including malleus 7, incus 8, and stapes 9), to the cochlea 4. The base or footplate of stapes 9 communicates auditory vibrations to the fluid in cochlea 4 via oval window 11. Residing within the cochlea 4 are hair cells (not shown) which convert the fluid vibrations into nerve impulses which are subsequently perceived by the brain as sound. During the process of converting vibration into nerve impulses, a portion of the hair cells "contract" and physically move. It is this movement or "mobility" which gives the mammalian ear extraordinary dynamic range by "amplifying" soft sounds more than loud sounds. As a consequence of the movement of the hair cells, small vibrations are generated in the fluid of the cochlea 4, which in turn are reflected 'backwards' through the oval window 11, ossicular chain 10 and tympanic membrane 6. These small vibrations, being emitted by the ear in response to auditory stimulation are known as Otoacoustic Emissions or OAE's. Although many times very small, with a sensitive microphone and signal processing, these vibrations can be measured and used to screen the hearing ability of the cochlea 4. One such system is taught in U.S. Pat. Nos. 4,374,526 and 4,884,447 issued to Kemp and to Kemp and Bray respectively.

The interaction of the tympanic membrane 6, ossicular chain 10, and the fluid in the cochlea 4 is a vibration transmission system. Variation of the components of this system will modify the transmission of vibrations, to and from the hair cells. Variations can be caused by several factors, one of which is the pressure within the cochlea 4. The change in cochlear pressure influences the stapes 9/cochlea 4 interface.

The characteristics of the OAE response changes with ICP, and thus can be used as a relative indicator of ICP. In the healthy ear, the pressure within the cochlea 4 is equivalent to the ICP. Both the endolymphatic sac 1 and the cochlear aqueduct 3 communicate pressure between the cranial spaces and the cochlea 4. As ICP varies, the pressure changes are communicated to the cochlear fluids via cochlear aqueduct 3 and endolymphatic sac 1, thereby influencing stapes 9 position and tension against its muscle and ligament attachment. These physical changes in the mechanical system of the ear affectthe input transmission of the stimulus as well as the reverse transmission of the OAE response. Thus the pressure within the cochlea 4 is a reflection of the ICP. Since OAEs are hearing based, this relationship will not exist in patients with greater than 30–40 dB senorineural loss at 1 kHz. Temporary or permanent conductive losses will also limit OAE signal. Also, muscle relaxants may reduce the tension on stapes 9 thus attenuating the ICP-OAE relationship. Similarly, if cochlear aqueduct 3 is plugged, the device will measure no changes in OAE transmission, and thus report that there was no change in ICP.

Any process or system which utilizes this vibration transmission system will be more or less sensitive to ICP changes reflected as changes in one or more of the system components. In most processes, such as normal hearing and measurements to assess hearing (such as OAE's and ABR's), changes in transmission characteristics are either easily ignored, or compensated for by the compliance of the process itself. The present invention concentrates on measuring, and quantifying the changes in transmission characteristics to determine changes in ICP.

An OAE response can be elicited by several modes of stimulation, two of which have become dominant—Transient Evoked Otoacoustic Emission (TEOAE) and Distortion Product Otoacoustic Emission (DPOAE). A TEOAE system introduces a wide band audio burst in the ear, then listens for the response, which occurs 4–20 milliseconds later. The signal-to-noise-ratio (SNR) of the system is enhanced by ensemble averaging the response synchronous to the stimulus, usually around 1000 samples in the average. Limitations in the repetition rate of the stimulus burst coupled with the rather large number of samples restrict a new measurement of the entire hearing spectrum approximately every minute. In contrast, a DPOAE system introduces two pure tones (f1 and f2) into the canal and listens for the response while the stimulus is being delivered. The emission in this case appears as the distortion product $(2f_1-f_2)$, and is easily separated from the stimulus tones using Fast Fourier Transform (FFT) signal processing techniques. DPOAE results (for a single $f_1/f_2$ combination) can be obtained in seconds. The present invention can use either of these stimulation modes.

In a first embodiment, measuring, and quantifying the changes in transmission characteristics to determine changes in ICP is accomplished by analyzing the phase in a DPOAE signal, after first validating the patency of the communication between the cerebral spaces and the cochlea, and ruling out distortion caused by unequalized middle ear pressure.

In another embodiment, a TPOAE signal is analyzed to determine the optimum OAE response frequency. The DPOAE distortion product $(2f_1-f_2)$ is then set to the optimum OAE response frequency according to the TPOAE analysis and frequencies $f_1-f_2$ are output accordingly. The changes in transmission characteristics are then measured and quantified to determine changes in ICP.

Figure 8:
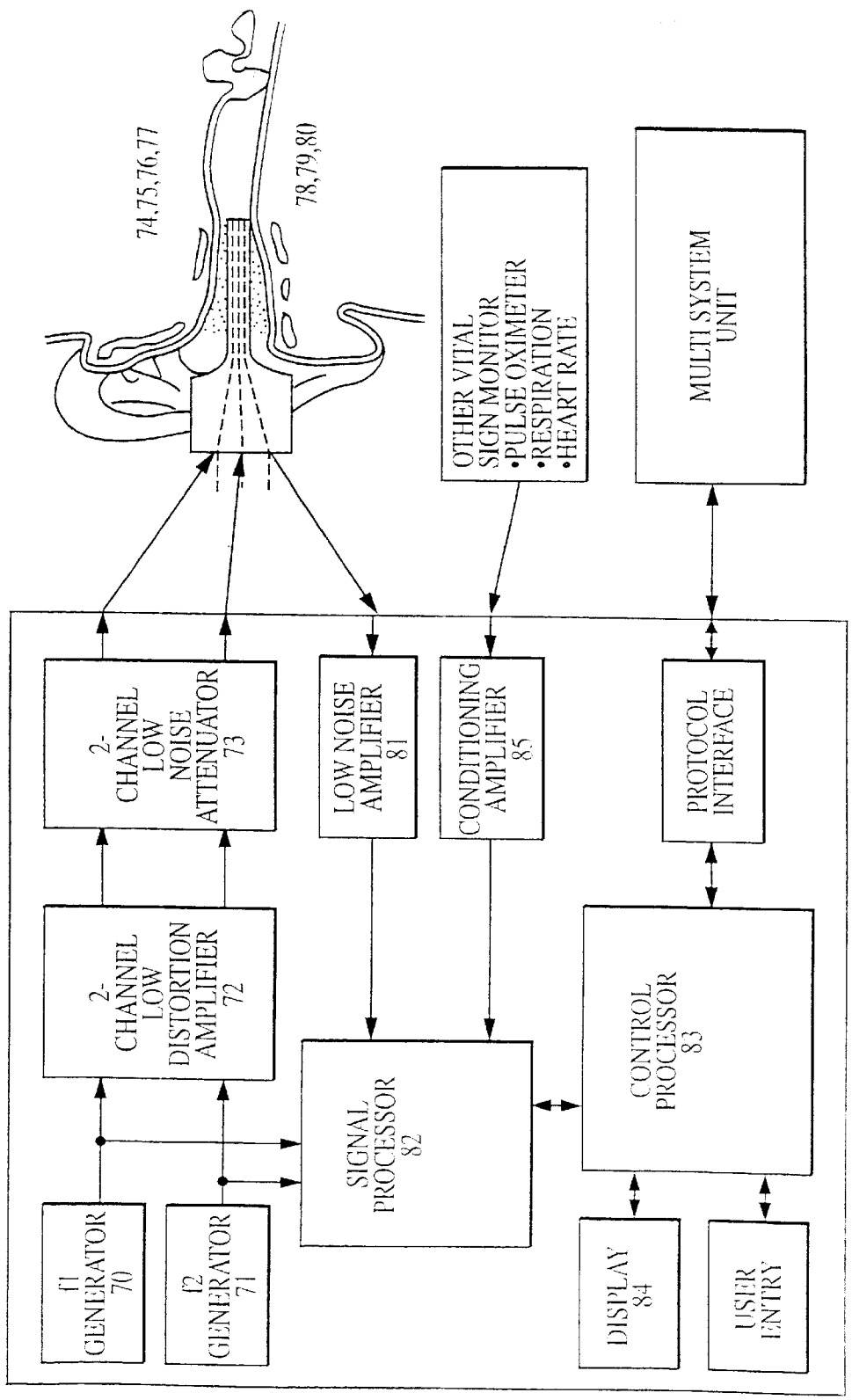
FIG. 8 is a flowchart of one method of operating the invention.

As seen in FIG. 8, first and second audio output generators 70 and 71 respectively are used to generate first and second frequencies, $f_1$ and $f_2$ respectively. The output levels of first and second audio output generators may be any level suitable for obtaining a $2f_1-f_2$ cochlear distortion. In one embodiment, the ratio of $f_2/f_1$ is 1.2 and the $2f_1-f_2$ frequency is below about 1 khz. Alternately, the ratio of the first and second audio output levels may be 6/5. In another embodiment, the distortion product $(2f_1-f_2)$ is set to the optimum OAE response frequency as determined by a TPOAE analysis. In one embodiment, this ratio is achieved by setting the first audio output level to 60 dB SPL and the second audio output to 50 dB SPL. First and second generators may further include rotating buffers. Optionally, first and second outputs are communicated through amplifier 72 and attenuator 73. Either directly after generation or after amplification and/or attenuation, first and second outputs are communicated to first and second output transducers, 74 and 75 respectively, within the patients external auditory canal.

The sound is reflected back as an otoacoustic signal emission of the cochlea. This OAE signal is the audio input used by the invention. Audio input transducer 76, including a $2f_1-f_2$ cochlear distortion, converts the audio input into a response signal. Optionally, the audio input transducer may be an acoustic microphone. In a first embodiment, first and second audio output transducers 74 and 75 and audio input transducer 76 are non-invasively coupled to the human auditory canal of the subject. The non-invasively coupling may be accomplished with a plug 77. Plug 77 may be manufactured of soft foam or soft plastic or any other suitable material. In one embodiment, the plug has three tubes, 78, 79 and 80, passing through it. The proximal end of each tube is connected to the first and second audio output generators and the distal end of each tube terminates in the auditory canal of the subject.

Signal processor 82 then processes the response signal to determine the intracranial pressure. Optionally, the response signal may be amplified by amplifier 81 before communication to the signal processor. In one embodiment, the intracranial pressure is processed further in control processor 83. Readings from other vital sign monitors, for example a pulse oximeter, respirator, or heart rate monitor, may be input into control monitor 83 (and optionally amplified by amplifier 85 prior to input). These readings may be interpreted in conjunction with the ICP value for additional information, for example, cerebral oxygenation or cerebral perfusion pressure. The intracranial pressure and other desired information is then displayed on display 83.

The response signal may be validated to ensure better ICP monitoring. A validation signal is generated to validate the response signal. The validation signal may be physiological (respiratory or cardiac, for example) or from an external source (from a respirator, kidney dialysis machine, or liver support machine, for example) In one embodiment, a respiration signal is generated representative of the inhalation and exhalation of the subject. The respiration signal may be generated using impedance plethsmography. Alternately, it may be an elastic sensor in contact with the chest of the subject or may be communication with a respirator party system. The signal processor isolates the $2f_1-f_2$ cochlear distortion signal from the response signal and measures the phase of the isolated $2f_1-f_2$ cochlear distortion signal to validate the relationship between the phase of the $2f_1-f_2$ cochlear distortion and the ICP of the subject. The isolation step may be performed with an FFT calculation wherein the FFT length, sample rate, $f_1$ and $f_2$ are advantageously chosen such that $2f_1-f_2$ frequency is represented by a single bin of the FFT calculation. In one embodiment, the phase measurement is the imaginary portion of the FFT calculation of the bind representative of the $2f_1-f_2$ frequency.

Validation of the result is almost as important as the result itself and is an important aspect of the first embodiment. The occurrence of a false negative, that is a reading of normal ICP when in reality it is elevated, could be fatal. To validate the patency of the cochlear aqueduct, the phase of the DPOAE signal is analyzed in concert with the respiration signal. At any ICP level, respiration should modulate the phase of the DPOAE. If it is not detected, either the patient's cochlear aqueduct is not patent, or, the patient has a ventropeneal shunt. In either case, this is indicated to the physician as an anomaly. In addition, the phase of the DPOAE is measured over the 2 Khz region. Unequalized middle ear pressure (ear 'popping' in an elevator or airplane) distorts the phase signal in the desired measurement region, and has a characteristic 'hump' in the 2 Khz region if the middle ear pressure is not equalized. Thus, it is advantageous to determine the presence of equalized middle ear pressure by verifying the absence of a phase hump in the 2 khz region.

After validation, the signal processor converts the phase to intracranial pressure. In one embodiment, the conversion is done with a formula calculation, for example, $\Delta ICP=(\Delta\phi \text{ (deg)})*5$. It may also be advantageous to calibrate the conversion mechanism. This calibration may be done by entering an absolute reading, by deriving a calibration from an invasive intracranial sensor, by changing the patient's posture, or by any other means suitable for calibration. If the patient's posture is changed, a particularly preferred method includes moving the patient from prone position to head tilted down 30°. The intracranial pressure may be displayed or printed for physician viewing.

Figure 1:
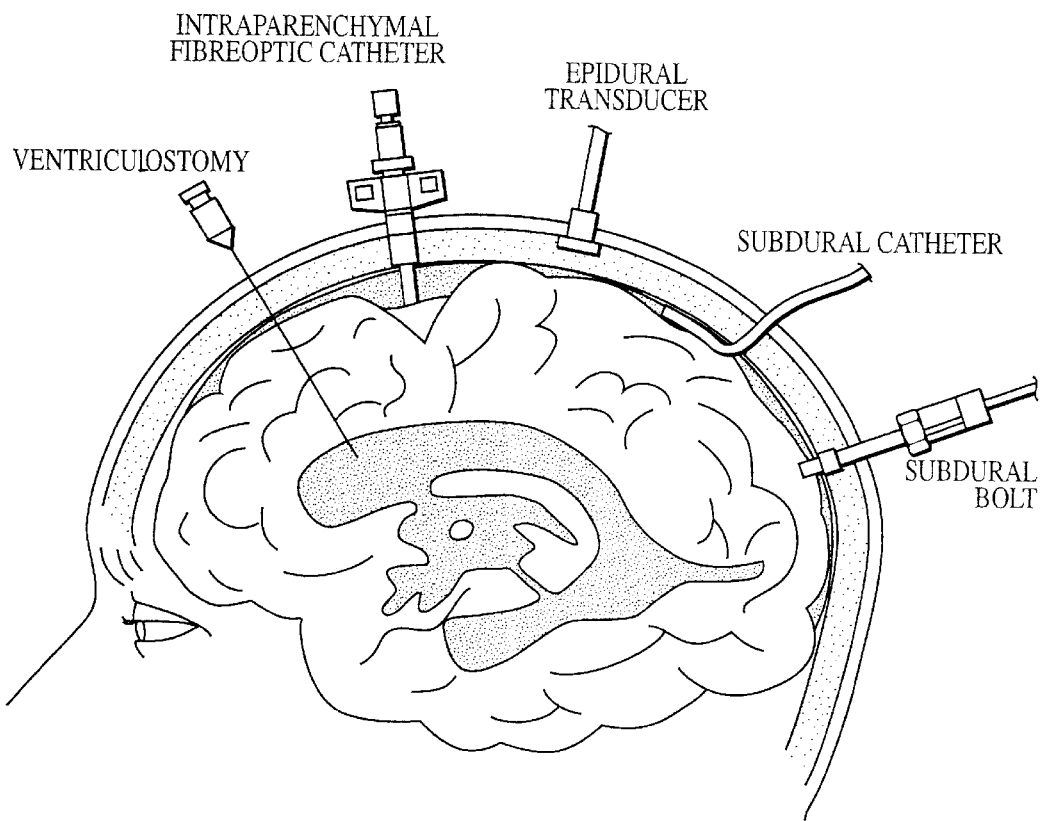
FIG. 1 is a drawing of three current invasive methods of measuring ICP.
Figure 2:
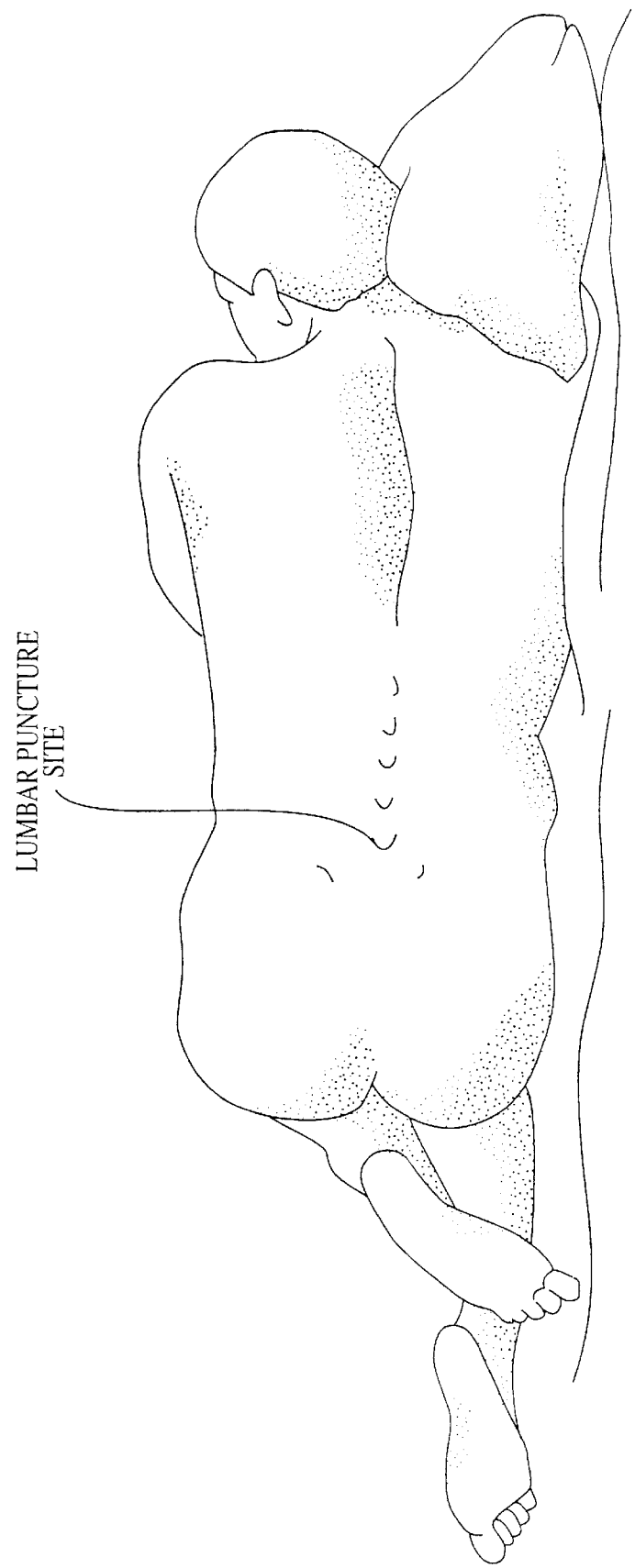
FIG. 2 is a drawing of another invasive method, a lumbar puncture, of measuring ICP.
Figure 3:
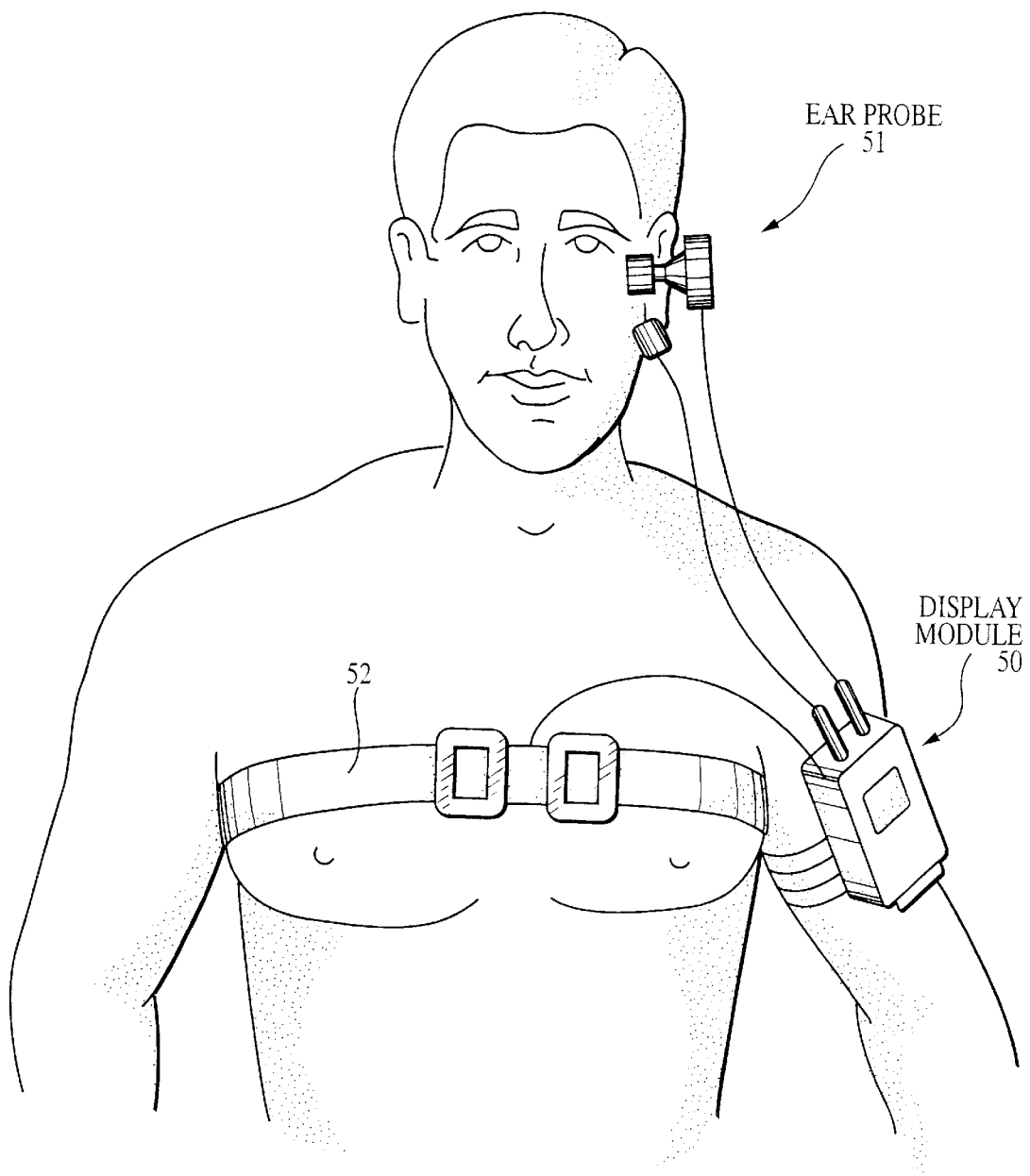
FIG. 3 is a drawing of one embodiment of the invention strapped to a patients arm.

As depicted in FIG. 3, in one embodiment of the invention, the electronics and display module may be housed in an arm-band display module 50. The display module is connected to ear probe 51 for insertion in the external auditory canal of the patient. Optionally, elastic sensor 52 in contact with the patient's chest may be used to monitor the patient's respiration in order to validate the intracranial pressure reading.

Figure 4:
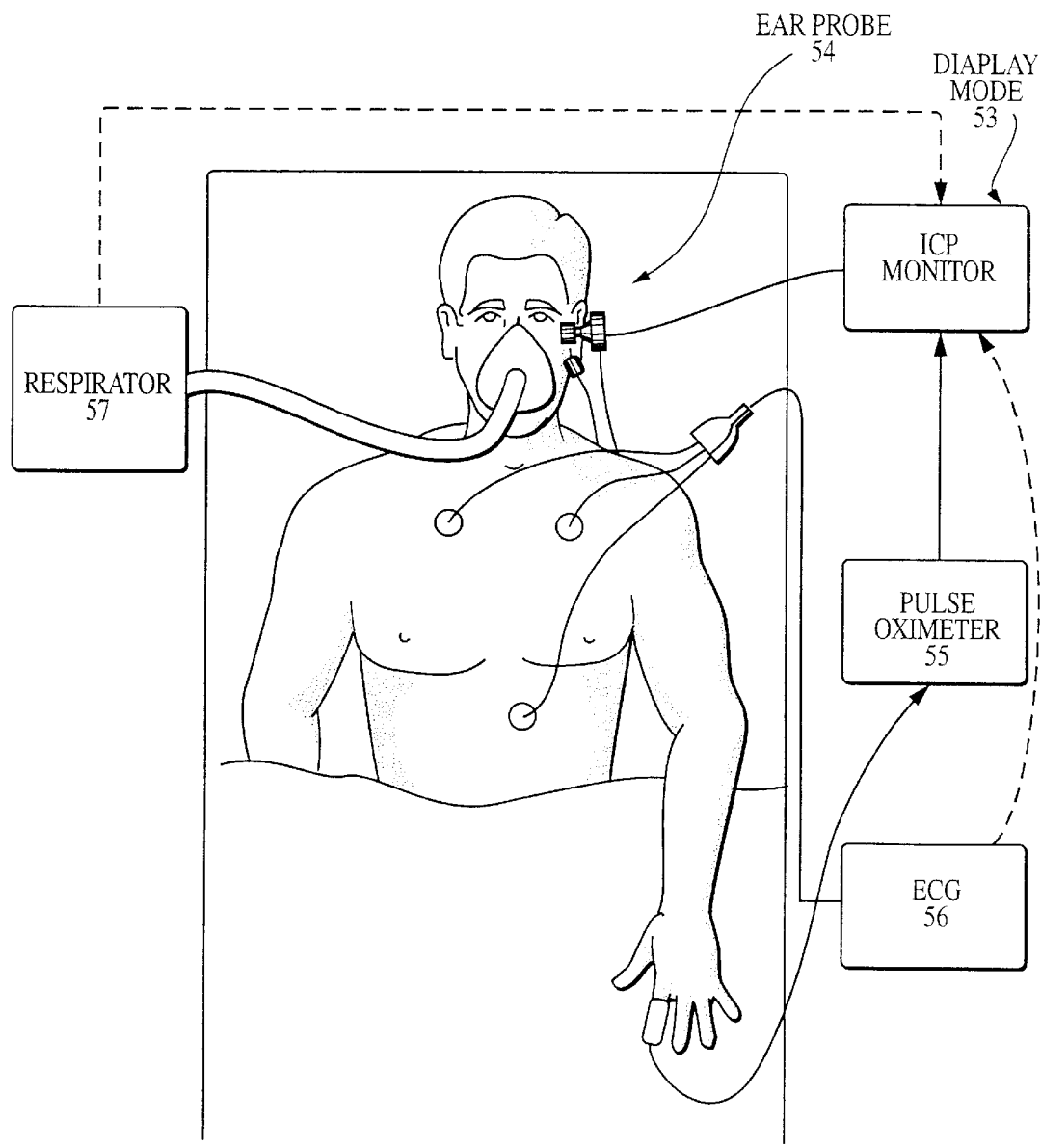
FIG. 4 is a drawing of a bedside embodiment of the invention.
Figure 5:
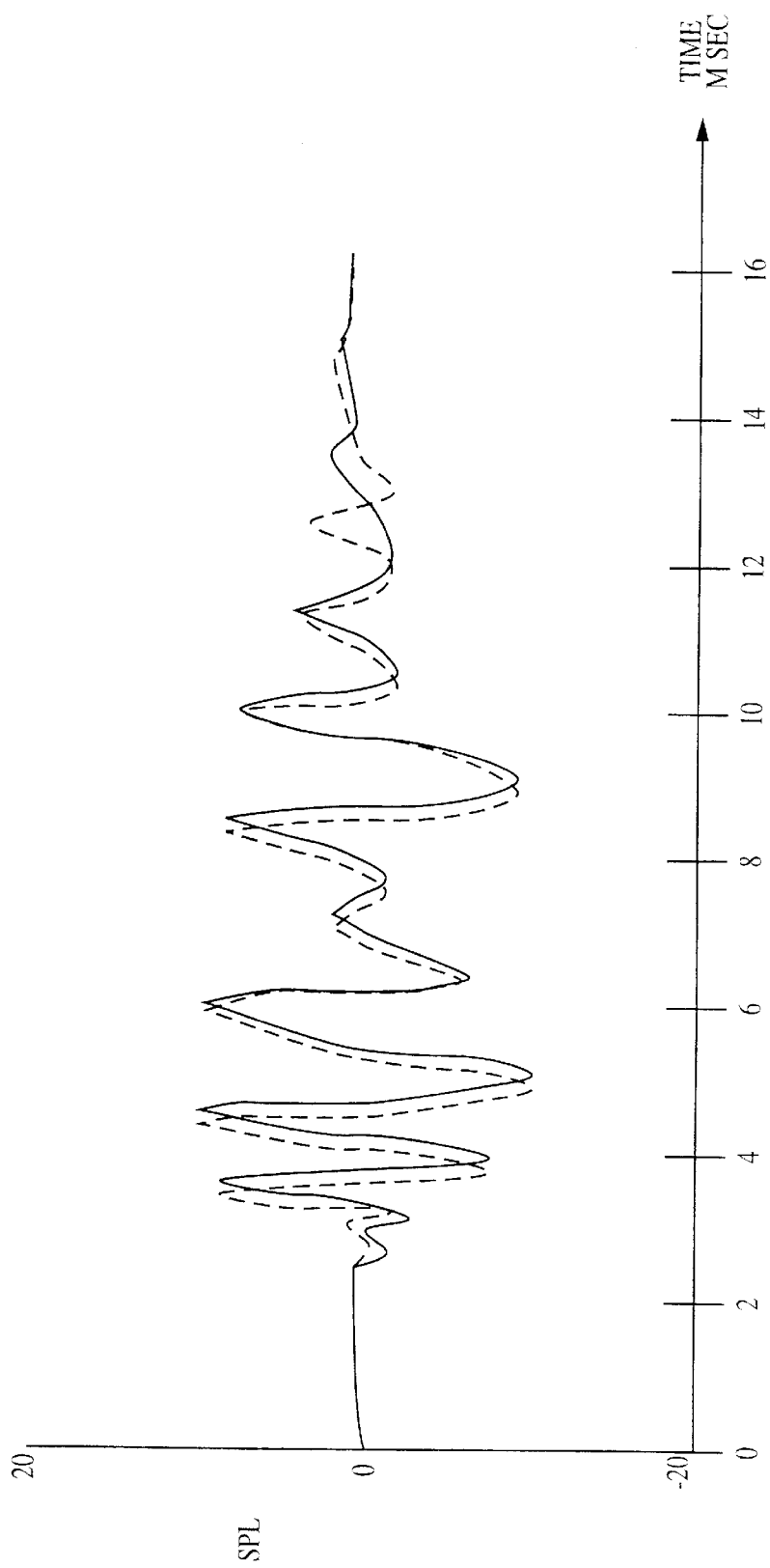
FIG. 5 is a graph typical TEOAE signal and the change in response to elevated ICP.
Figure 6:
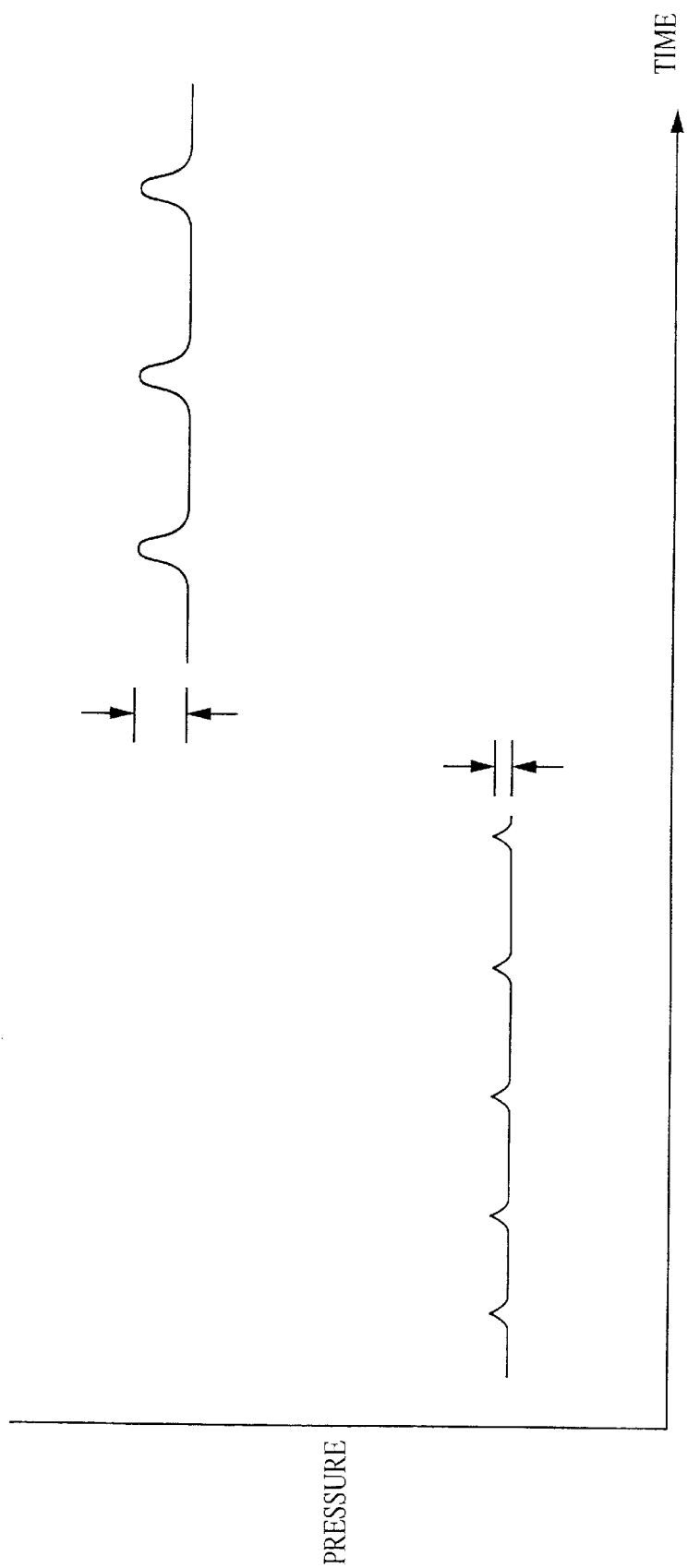
FIG. 6 is a graph of respiration modulating the ICP signal at two distinct absolute pressures.

FIG. 4 depicts an alternate embodiment of the invention wherein the display module 53 is bedside. Display module 53 is connected to ear probe 54. Ear probe 54 is configured for insertion into patient's external auditory canal. Optionally, the display module may be in contact with pulse oximeter 55, ECG 56, or respirator 57 for further quantifying the intracranial pressure data.

While particular embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A method for continuous non-invasive monitoring of intracranial pressure of a subject comprising the steps of:
   a) outputting a first audio output of frequency $f_1$ with a first audio output transducer;
   b) outputting with a second audio output transducer a second audio output of frequency $f_2$, wherein $f_2$ is greater than $f_1$;
   c) receiving and converting an audio input into a response signal with an audio input transducer including a $2f_1-f_2$ cochlear distortion;
   d) non-invasively coupling the first and second audio output transducers and the audio input transducer with the human auditory canal of the subject;
   e) receiving a validation signal for validating the phase of the cochlear distortion signal and intra-cranial pressure of the subject;
   f) processing the response signal and the validation signal with a signal processor to determine the intracranial pressure of the subject;
   g) displaying the intracranial pressure.

2. The method of claim 1 wherein the audio input is the otoacoustic emission signal of the cochlea.

3. The method of claim 1 further including the step of generating a further validation signal.

4. The method of claim 3 and wherein the processing step further includes the steps of:
   a) isolating the $2f_1-f_2$ cochlear distortion signal from the response signal;
   b) measuring the phase of the isolated $2f_1-f_2$ cochlear distortion signal;
   c) validating the relationship between the phase of the isolated $2f_1-f_2$ cochlear distortion signal and intracranial pressure of the subject, and
   d) converting the phase to intracranial pressure.

5. The method of claim 4 wherein the validating step further includes the step of generating a validation signal in the phase of the $2f_1-f_2$ frequency.

6. The method of claim 1 wherein the validation signal is a physiological signal.

7. The method of claim 6 wherein the physiological signal is a respiration signal representative of the inhalation and exhalation of the subject.

8. The method of claim 7 wherein the respiration signal is generated using impedance plethsmography.

9. The method of claim 7 wherein the respiration signal is generated with a signal from an artificial respirator in contact with the subject.

10. The method of claim 7 wherein the respiration signal is generated with an elastic sensor in contact with the chest of the subject.

11. The method of claim 6 wherein the physiological signal is a cardiac signal.

12. The method of claim 5 wherein the validation signal is an externally produced signal.

13. The method of claim 12 wherein the externally produced signal is a produced by a respirator.

14. The method of claim 12 wherein the externally produced signal is produced by a kidney dialysis machine.

15. The method of claim 12 wherein the externally produced signal is produced by a liver support machine.

16. The method of claim 4 wherein the validating step further includes the step of determining the presence of equalized middle ear pressure by verifying the absence of a phase hump in the 2 khz region.

17. The method of claim 1 wherein $2f_1-f_2$ cochlear distortion signal is isolated with a fast fourier transformer (FFT calculation), wherein the FFT length, sample rate, $f_1$ and $f_2$ are advantageously chosen such that the $2f_1-f_2$ frequency is represented by a single bin of the FFT calculation.

18. The method of claim 17 wherein the phase measurement is atan(Im/Re).

19. The method of claim 1 wherein the ratio of $f_2/f_1$ is 1.2 and the $2f_1-f_2$ frequency is below about 1 khz.

20. The method of claim 19 wherein the first audio output is set to 60 dB SPL and the second audio output is set to 50 dB SPL.

21. The method of claim 1 wherein the ratio of the first and second audio output levels is 6/5.

22. The method of claim 1 further comprising the steps of generating an output burst and interpreting the OAE response of the output burst to determine the patient's optimum OAE response frequency.

23. The method of claim 22 wherein the distortion product $(2f_1-f_2)$ is set to the optimum OAE response frequency.

24. The method of claim 1 wherein the converting step further includes a formula calculation.

25. The method of claim 24 wherein the formula is set to $\Delta ICP=(\Delta\phi(deg))*5$.

26. The method of claim 1 wherein the receiving and converting step further includes the step of calibrating the phase measurement.

27. The method of claim 26 wherein the calibration step comprises the step of entering an absolute reading.

28. The method of claim 26 wherein the calibration step comprises the step of deriving a calibration from an invasive intracranial sensor.

29. The method of claim 28 wherein changing the patient's posture comprises the step of moving the patient from supine position to head tilted down 30°.

30. The method of claim 26 wherein the calibration step comprises the step of changing the patient's posture.

31. The method of claim 1 further comprising the steps of characterizing and quantifying the intracranial pressure based on an ICP reading taken by an invasive pressure transducer.

32. The method of claim 1 further including the steps of monitoring a second patient physiological signal and quantifying the intracranial pressure data in conjunction with the second signal.

33. The method of claim 1 further including the step of estimating cerebral oxygenation by interpreting the intracranial pressure in conjunction with the readings from a pulse oximeter.

34. The method of claim 1 further including the step of estimating cerebral perfusion pressure by interpreting the intracranial pressure in conjuction with the blood pressure.

35. The method of claim 1 further including the steps of measuring the intracranial pressure in both ears of a patient to provide hemispheric information.

36. A method of treating a stroke comprising the method of claim 1 to determine the intracranial pressure and further comprising the steps of comparing the intracranial pressure measurement with a predetermined value and diagnosing the stroke type.

37. A method of treating a patient on liver support comprising the method of claim 1 to determine the intracranial pressure and further comprising the steps of comparing the intracranial pressure measurement with a predetermined value; and, if the intracranial pressure measurement exceeds the predetermined value, of recommending liver therapy.

38. A method of treating a patient who has been shunted to control intra-cranial pressure comprising the method of claim 1 to determine the intracranial pressure and further comprising the steps of comparing the intracranial pressure measurement with a predetermined value.

39. A method of treating a patient on kidney dialysis comprising the method of claim 1 to determine the intracranial pressure and further comprising the steps of comparing the intracranial pressure measurement with a predetermined value; and, if the intracranial pressure measurement exceeds the predetermined value, of recommending dialysis.

40. A method for continuous non-invasive monitoring of intracranial pressure of a subject comprising the steps of:
  a) generating a first audio output of frequency $f_1$ with a first audio output generator;
  b) generating a second audio output of frequency $f_2$, wherein $f_2$ is greater than $f_1$;
  c) communicating first and second audio outputs to a first and a second transducer;
  d) outputting first and second outputs with first and second transducers;
  e) receiving and converting an audio input into a response signal with an audio input transducer including a $2f_1-f_2$ cochlear distortion;
  f) non-invasively coupling first and second audio output transducers and transducer with the human auditory;
  g) processing the response signal and a validation signal with a signal processor to determine the intracranial pressure of the subject, such processing further including the steps of
    i. isolating the $2f_1-f_2$ cochlear distortion signal from the response signal;
    ii. measuring the phase of the isolated $2f_1-f_2$ cochlear distortion signal; and
    iii. converting the phase to intracranial pressure; and
  h) generating said validation signal for validating the relationship between the phase of the isolated 2f-f cochlear distortion signal and intracranial pressure of the subject, and
  i) displaying the intracranial pressure.

41. The method of claim 40 further comprising the steps of amplifying and attenuating the first and second outputs before communicating the first and second outputs to the first and second output transducers.

42. The method of claim 40 further comprising the step of amplifying the response signal prior to signal processing.

43. An apparatus for continuous non-invasive monitoring of intracranial pressure of a subject comprising:
  a) a first audio output transducer to output frequency $f_1$;
  b) a second audio output transducer to output frequency $f_2$, wherein $f_2$ is greater than $f_1$;
  c) an audio input transducer for converting an audio input into a response signal having a $2f_1-f_2$ cochlear distortion, wherein the audio input is the otoacoustic emission signal of the cochlea;
  d) a non-invasive coupling between the first and second audio output transducers and the audio input transducer and the auditory canal of the subject;
  e) a signal generator for generating a validation signal for validating the relationship between the phase of the cochlear distortion signal and intracranial pressure of the subject, f) a signal and the validation signal processor to process the response signal to determine the intracranial pressure of the subject; and g) a display for displaying intracranial pressure.

44. The apparatus of claim 43 wherein the signal generator is an artificial respirator in contact with the subject.

45. The apparatus of claim 44 wherein the artificial respirator is wireless.

46. The apparatus of claim 45 wherein the generator is an elastic sensor in contact with the chest of the subject.

47. The apparatus of claim 44 wherein the physiological signal is a cardiac sensor.

48. The apparatus of claim 44 further comprising a generator for generating a validation signal.

49. The apparatus of claim 43 wherein the generator generates an external signal.

50. The apparatus of claim 49 wherein the generator is a respirator.

51. The apparatus of claim 49 wherein the generator is a kidney dialysis machine.

52. The method of claim 49 wherein the generator is a liver support machine.

53. The apparatus of claim 43 wherein the signal processor isolates the $2f_1-f_2$ cochlear distortion signal from the response signal; measures the phase of the isolated $2f_1-f_2$ cochlear distortion signal, validates the relationship between the phase of the isolated $2f_1-f_2$ cochlear distortion signal and intracranial pressure of the subject, and converts the phase to intracranial pressure.

54. The apparatus of claim 53 wherein the signal processor further comprises a position sensor to compensate for position effect on intracranial pressure to validate the relationship between the phase of the isolated $2f_1-f_2$ cochlear distortion signal and the intracranial pressure of the subject.

55. The apparatus of claim 54 wherein the position sensor is an accelerometer.

56. The apparatus of claim 53 wherein the signal processor further comprises a preset lookup table for converting the phase of the isolated $2f_1-f_2$ cochlear distortion signal to intracranial pressure.

57. The apparatus of claim 53 further configured for insertion into a standard ambulatory monitor.

58. The apparatus of claim 57 wherein the audio input transducer is an acoustic microphone.

59. The apparatus of claim 58 wherein the non-invasive coupling is a plug comprising a cylindrical device having three tubes, each having a proximal and a distal end, passing through the device, the proximal end of each tube is connected to the first and second audio output transducers, and the distal end of each tube being configured for placement in the auditory canal of the subject.

60. The apparatus of claim 43 wherein the plug is constructed of soft foam.

61. The apparatus of claim 43 wherein the plug is molded of soft plastic.

62. The apparatus of claim 55 wherein the signal process further comprises a calibrator for converting the phase of the isolated $2f_1-f_2$ cochlear distortion signal to intracranial pressure.

63. The apparatus of claim 61 wherein the calibrator further comprises an invasive intracranial sensor.

64. The apparatus of claim 43 wherein the calibrator further comprises a stored template.

65. The apparatus of claim 43 further configured for use as a continuous bedside monitor.

66. The apparatus of claim 43 further configured for use as a portable monitor.

67. The apparatus of claim 43 further configured for use with a telephone follow-up system.

68. The apparatus of claim 43 further comprising a noise canceling system to enhance the signal to noise ratio of the OAE signal.

69. An apparatus for continuous non-invasive monitoring of intracranial pressure of a subject comprising:

a) a first audio output generator to generate frequency $f_1$;

b) a second audio output generator to generate frequency $f_2$, wherein $f_2$ is greater than $f_1$;

c) first and second audio output transducers in communication with first and second audio output generators;

d) an audio input transducer for converting an audio input into a response signal having a $2f_1-f_2$ cochlear distortion, wherein the audio input is the otoacoustic emission signal of the cochlea;

e) a signal processor to process the response signal and a respiration validation signal to determine the intracranial pressure of the subject; and f) a display for displaying intracranial pressure.

70. The apparatus of claim 69 further comprising an amplifier and an antenuator between first and second audio output generators and first and second audio output transducers.

71. The apparatus of claim 70 further comprising a non-invasive coupling integrated with the first and second audio output transducers, and audio input transducer coupled with the auditory canal of the subject.

72. The apparatus of claim 70 wherein the non-invasive coupling is further integrated with the antenuator.

73. The apparatus of claim 69 further comprising an amplifier between the audio input transducer and the signal processor.

74. The apparatus of claim 69 wherein first and second output generators and signal processor each further comprise a buffer.

75. An apparatus for continuous non-invasive monitoring of intracranial pressure of a subject comprising:

a) an audio output burst generator;

b) a first audio input transducer for converting an audio input into a response signal wherein the audio input is the otoacoustic emission of the cochlea in response to an audio output burst;

c) a processor for processing the output burst response signal and determining the optimum OAE response frequency, $f_{opt}$, of the patient;

d) a first audio output transducer to output frequency $f_1$;

e) a second audio output transducer to output frequency $f_2$, wherein $f_2$ is greater than $f_1$; and $2f_1-f_2$ is equal to $f_{opt}$;

f) a second audio input transducer for converting an audio input into a distortion response signal having a $2f_1-f_2$ cochlear distortion, wherein the audio input is the otoacoustic emission signal of the cochlea in response to first and second audio outputs;

g) a signal processor to process the distortion response signal and convert the response signal into the intracranial pressure of the subject; and h) a display for displaying intracranial pressure.

76. The apparatus of claim 75 wherein first and second audio input transducers are the same transducer.

77. The apparatus of claim 75 further comprising a non-invasive coupling for coupling first and second audio output transducers and second audio input transducer with the auditory ear canal of the subject.

78. The apparatus of claim 77 wherein the non-invasive coupling further couples the output burst generator and first audio input transducer with the auditory ear canal of the subject.

79. The apparatus of claim 75 wherein the audio output bursts generates a spectrum that is optimally flat from about 500 to 3000 Hz.

80. The apparatus of claim 75 further comprising a generator for generating a validation signal.

81. The apparatus of claim 80 wherein the signal processor isolates the $2f_1-f_2$ cochlear distortion signal from the distortion response signal; measures the phase of the isolated $2f_1-f_2$ cochlear distortion signal, validates the relationship between the phase of the isolated $2f_1-f_2$ cochlear distortion signal and intracranial pressure of the subject, and converts the phase to intracranial pressure.

* * * * *